United States Patent
Strange et al.

(10) Patent No.: US 6,815,306 B1
(45) Date of Patent: Nov. 9, 2004

(54) FLOATING ANODE DC ELECTROLYTIC CAPACITOR

(75) Inventors: Thomas F. Strange, Easley, SC (US); Timothy R. Marshall, Pickens, SC (US); Thomas V. Graham, Greenville, SC (US)

(73) Assignee: Pacesetter, Inc., Sunnyvale, CA (US)

(*) Notice: Subject to any disclaimer, the term of this patent is extended or adjusted under 35 U.S.C. 154(b) by 499 days.

(21) Appl. No.: 10/075,711

(22) Filed: Feb. 13, 2002

Related U.S. Application Data

(62) Division of application No. 09/668,018, filed on Sep. 21, 2000, now Pat. No. 6,377,442.

(51) Int. Cl.[7] ............................. H01L 21/20; H01G 9/00
(52) U.S. Cl. ...................... 438/379; 438/171; 438/190; 438/238; 361/503; 361/502
(58) Field of Search ................................. 438/379, 190, 438/171, 210, 238, 239; 361/502, 503, 504, 506, 508, 509, 510, 512, 516, 523, 526, 531

(56) References Cited

U.S. PATENT DOCUMENTS

| | | | |
|---|---|---|---|
| 5,131,388 A | | 7/1992 | Pless et al. .............. 128/419 D |
| 5,786,980 A | * | 7/1998 | Evans ......................... 361/502 |
| 5,930,109 A | | 7/1999 | Fishler ....................... 361/508 |

* cited by examiner

*Primary Examiner*—David Nelms
*Assistant Examiner*—Long Tran
(74) *Attorney, Agent, or Firm*—Steven M. Mitchell

(57) ABSTRACT

The present invention is directed to an electrolytic capacitor having a novel floating anode between the cathode and the powered anode of the capacitor, resulting in a single capacitor having a working voltage double that of the formation voltage of the powered anode. The floating anode acts as cathode to the powered anode and as an anode to the cathode, such that the capacitor according to the present invention supports half the working voltage between the cathode and the floating anode and half the working voltage between the floating anode and the powered anode. The arrangement of the cathode, floating anode and powered anode according to the present invention results in a single capacitor with half the capacitance and twice the voltage of a single anode device.

6 Claims, 2 Drawing Sheets

FLOATING ANODE DC ELECTROLYTIC CAPACITOR

This is a divisional of application Ser. No. 09/668,048, filed on Sep. 21, 2000, now U.S. Pat. No. 6,377,442.

BACKGROUND OF THE INVENTION

1. Field of the Invention

The present invention is directed to an electrolytic capacitor, and more particularly to an electrolytic capacitor having a novel floating anode between the cathode and the powered anode, resulting in a single capacitor with a working voltage double that of the anode formation voltage.

2. Related Art

Capacitors are energy storage devices usually consisting of two conducting surfaces (plates) separated by an insulator (the dielectric). When voltage is applied to the capacitor plates, an electrical field is created between them. The strength of the electrical field is directly proportional to the voltage on the plates and inversely proportional to the distance between them. The ability of the plates to hold opposite and equal charges when a voltage is applied to them is termed capacitance.

Compact, high voltage capacitors are utilized as energy storage reservoirs in many applications, including implantable medical devices. These capacitors are required to have a high energy density since it is desirable to minimize the overall size of the implanted device. This is particularly true of Implantable Cardioverter Defibrillators (ICDs), also referred to as implantable defibrillators, since the high voltage capacitors used to deliver the defibrillation pulse can occupy as much as one third of the ICD volume.

Electrolytic capacitors (either wound roll or flat) are commonly used in ICDs, because they have the most ideal properties in terms of size, reliability and ability to withstand relatively high voltage. Aluminum electrolytic capacitors, having plates comprised of aluminum foil, are the most common type currently employed in implantable defibrillators. However foils of other conventional valve metals such as titanium, tantalum, magnesium, niobium, zirconium and zinc can also be used. Conventional electrolytic capacitors are constructed with a powered anode foil plate at a positive potential with respect to a negatively charged cathode foil plate. The anode foil is typically roughened or etched to enhance surface area and a barrier oxide layer is formed continuously over the anode foil surface to support the intended voltage. This oxide layer is the dielectric of the electrolytic capacitor. The powered anode and cathode are separated by a kraft paper or fabric gauze separator impregnated with a solvent-based liquid electrolyte. The separator material impregnated with the liquid electrolyte in conjunction with the negatively charged cathode foil functions as the negative terminal of the capacitor. A typical solvent-based liquid electrolyte may be a mixture of a weak acid and a salt of a weak acid, preferably where the salt is the salt of the same weak acid, employed in a polyhydroxy alcohol solvent. Typically, the electrolytic or ion-producing component of the electrolyte is the salt that is dissolved in the solvent.

In the case of a cylindrical or wound roll electrolytic capacitor, the surface area of the foils are made as large as possible by employing very thin rolls of foil that can be compactly rolled into a relatively small volume. The formed foil is rolled and then "aged" in the presence of an electrolyte to grow oxide on any exposed aluminum. Aging is the process of slowly increasing the voltage on the capacitor after impregnation with electrolyte over the course of many hours by charging the capacitor using a small current source. After reaching the maximum rated voltage, the voltage is decreased and the temperature increased. The entire laminate is rolled up into the form of a substantially cylindrical body, or wound roll that is held together with adhesive tape and is encased, with the aid of suitable insulation, in an aluminum tube or canister. Connections to the anode and the cathode are made via tabs. Further details of the construction of such traditional high voltage capacitors used in ICDs are described by P. J. Troup, "Implantable Cardioverters and Defibrillators," at pp. 704–713 (Current Problems in Cardiology, Vol. XIV, No. 12, December 1989, Year Book Medical Publishers, Chicago), which pages are incorporated herein by reference.

Alternative flat constructions for electrolytic capacitors are also known, composing a planar, layered, stack structure of electrode materials with separators interposed therebetween. An ICD with flat geometry electrolytic capacitors is described in U.S. Pat. No. 5,131,388 to Pless et al., which is incorporated herein by reference in its entirety.

The maximum rated working voltage of readily available electrolytic capacitors is in the range of 600 V. Consequently, conventional ICDs use two 350 to 450 V capacitors in series to achieve the desired high voltage for shock delivery, in the range of 700 to 900 V. In this arrangement, approximately 3 joules of energy can be stored per cubic centimeter of capacitor volume, making the capacitor the single largest limitation to further miniaturization of implantable defibrillators. From the standpoint of size, it would be desirable to provide a capacitor arrangement for an ICD in a single package rather than two capacitors in series. Thus, what is needed is a capacitor arrangement for an ICD in a single package capable of operating at a voltage of 700 to 900 volts.

SUMMARY OF THE INVENTION

The present invention is directed to an electrolytic capacitor having a novel floating anode between the cathode and the powered anode of the capacitor, resulting in a single capacitor having a working voltage double that of the formation voltage of the powered anode. The floating anode acts as cathode to the powered anode and as an anode to the cathode, such that the capacitor according to the present invention supports half the working voltage between the cathode and the floating anode and half the working voltage between the floating anode and the powered anode.

The arrangement of the cathode and anode plates according to the present invention results in a single capacitor with half the capacitance and twice the voltage of a single anode device. The capacitance lost is more than made up for by using a lower formation voltage anode foil. Additionally, the advantage of a single package and the improvement achieved using foil formed to half the intended voltage greatly outweighs the small energy density penalty for the extra thickness created by the additional anode and separator paper. For example, a foil suitable for 400 volt operation may have a maximum capacitance of 0.8 $\mu F/cm^2$ and is readily obtainable. The best foil suitable for 800 volt operation obtainable on the market, however, will have a capacitance no more than 0.2 $\mu F/cm^2$. By using two 0.8 $\mu F/cm^2$ foils, one as the powered anode and one as the floating anode according to the present invention, the resulting capacitance for the combination is 0.4 $\mu F/cm^2$, twice the 0.2 $\mu F/cm^2$ capacitance obtained for the foil suitable for 800 V operation. Additionally, this design is advantageous in that it will assemble in one package, giving some volume savings over two 400 V capacitors in series.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

The following disclosure is directed to an electrolytic capacitor having a novel floating anode between the cathode and the powered anode and a method for making such a capacitor. This arrangement results in a single capacitor having a working voltage double that of the formation voltage of the powered anode and solves the need for a capacitor arrangement for an ICD in a single package capable of operating at a voltage of 700 to 900 volts.

Figure 1:
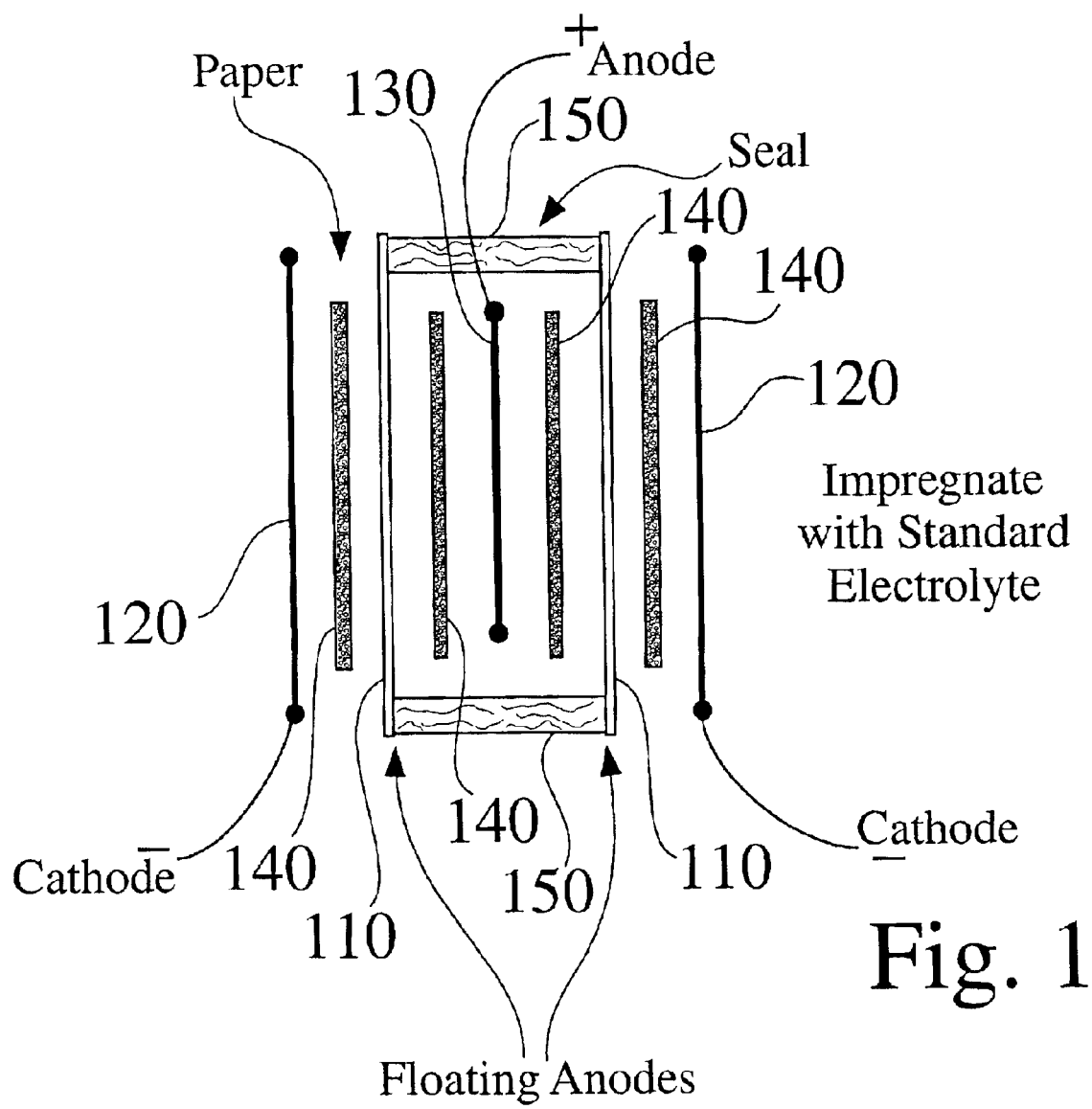
FIG. 1 is a schematic diagram of an electrolytic capacitor according to the present invention.

Referring now to FIG. 1, a schematic view of a capacitor according to the present invention is shown. Specifically, the device consists of a floating anode 110 disposed between a cathode 120 and a powered or working anode 130, with separators 140, impregnated with a standard electrolyte, interposed therebetween. The capacitor according to the present invention incorporating the distinct feature of a floating anode can be rolled, stacked, accordioned, or spiraled, as known to those skilled in the art. Connections to the powered anode and the cathode can be made via tabs or other means known to those skilled in the art. Alternatively, the floating anode can be externally or internally tied to the powered anode by a voltage divider, or source center tap, to regulate the voltage drop percentages and thus tailor the floating anode arrangement for optimum performance.

Each anode layer may consist of a single anode plate, double anode plates, or a higher number of anode plates, as know to those skilled in the art. Each configuration will give a different energy density and different ESR. ESR is the equivalent series resistance which should be as low as possible or at least matched to the application. Energy density gets better as the number of anode plates per layer increases, but ESR gets worse (i.e., gets higher). The actual number of anode plates per layer will therefore be a compromise between a lower energy density and an acceptable ESR, with two anode plates in common use for these and similar applications.

Each powered anode plate 130 is highly etched on both sides to increase surface area. Similarly, each floating anode plate 110 is also etched on both sides to increase surface area. By etching the surface of the anode foils, the surface area and the capacitance are increased accordingly. As is known to those skilled in the art, the capacitance of the electrolytic capacitor varies directly with the surface area of the anode electrode. Kraft paper or fabric gauze separators 140 or the like, impregnated with a solvent-based liquid electrolyte, cover-each anode layer and separate each anode layer from adjacent cathode plates. A typical solvent-based liquid electrolyte may be a mixture of a weak acid and a salt of a weak acid, preferably where the salt is the salt of the same weak acid, employed in a polyhydroxy alcohol solvent, however other solvent-based liquid electrolytes may be used as would be apparent to those skilled in the art without departing from the scope of the present invention.

According to the present invention, the working voltage is dropped across powered anode 130, and floating anode 110, to cathode 120, resulting in a single capacitor having a working voltage double that of the formation voltage of the powered anode. Floating anode 110 acts as cathode to powered anode 130 and as an anode to cathode 120, such that the capacitor according to the present invention supports half the working voltage between cathode 120 and floating anode 110 and half the working voltage between floating anode 110 and powered anode 130. This effectively results in a two capacitors in series arrangement, however in a single package.

Floating anode 110 must support half the total voltage on the side facing cathode 120, and must have a barrier oxide formed on this side. The side facing powered anode 130 does not need to support voltage and should not be formed, as this would result in a lower capacitance. The edges of anodes 110 and 130 are sealed, by hot glue seal 150 or by other methods known to those skilled in the art, such that powered anode 130 cannot directly "see" cathode 120 and form a shortened impedance path around floating anode 110, rendering floating anode 110 ineffective and causing extra oxide formation on powered anode 130 and loss of capacitance. To maintain this seal, floating anode 110 must not be porous. Alternatively, the nonporous floating anode could be replaced with a porous anode (as 130) welded as a laminate to a nonporous cathode (as 120), such that the unit would support voltage on one side but provide a high gain cathode on the other side. In this case, one side of the cathode would have to be formed to support half the total working voltage. Alternatively, a nonporous, non-symmetrical foil, which is etched and formed to act as an anode on one side and etched to act as a cathode on the other side, could be used in lieu of floating anode (110). These arrangements allow for the use of the higher gain porous anode foil for the recovery of capacitance lost in the nonporous arrangement.

In the preferred embodiment, a standard 300 $\mu$F porous anode foil 9 (allowing 23 ml of $H_2O$ to pass in 100 seconds) is used as powered anode 130, a 20 $\mu$m nonporous cathode foil (no $H_2O$ seepage in 100 sec) is used as cathode 120 and a nonporous, high strength, high voltage anode foil (no $H_2O$ seepage in 100 sec) is used as floating anode 110. The units are encased in a 110 $\mu$m Aluminum casing, sealed with hot glue.

The 800 V powered anode/floating anode/cathode design according to the present invention will assemble in one package giving significant volume savings over the conventional two 400 V capacitors in series arrangement.

Figure 2:
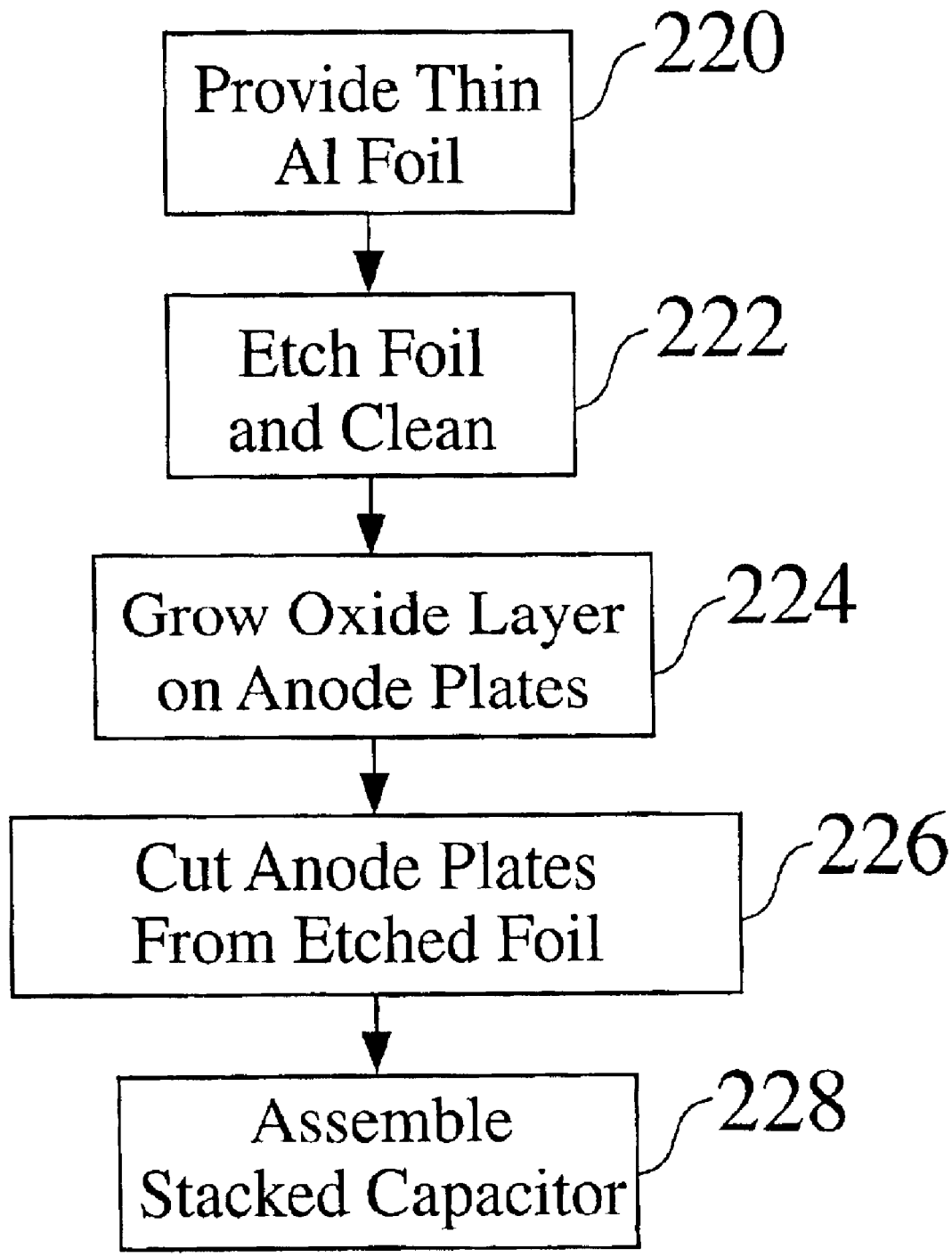
FIG. 2 is a process diagram illustrating the steps of the invention in producing an improved capacitor.

As discussed above, the capacitor according to the present invention incorporating the distinct feature of a floating anode can be rolled, stacked, accordioned or spiraled, as know to those skilled in the art. FIG. 2 is a process diagram illustrating a method of producing a stacked or flat capacitor according to the present invention. A sheet of thin high purity aluminum or other valve metal anode foil, from which a plurality of anode plates will be punched, is provided at step 220. In the preferred embodiment, the foil is about 2 to 10 mils thick. Aluminum is preferred; however, any of the conventional valve metals, such as titanium, tantalum, magnesium, niobium, zirconium and zinc may also be used.

The aluminum foil is then roughened or highly etched at step 222 to increase surface area, as described in U.S. Pat. No. 5,660,737, incorporated herein by reference. For purposes of the present invention, other etch processes known in the art could be used without departing from the scope of the present invention and the particular etch process used is not a part of the present invention. The etched foil is preferably cleaned with deionized (DI) water after the etch step.

After the anode foil is etched and cleaned, the anode plates are ready for forming, which involves growing an oxide layer on the etched anode foil surface at step 224. This is typically done by applying a voltage (formation voltage of 400 V) to the foil through an electrolyte such as boric acid or citric acid and water or other solutions familiar to those skilled in the art, resulting in the formation of aluminum oxide ($Al_2O_3$) on the surface of the anode plate. The thickness of aluminum oxide deposited or "formed" on the anode foil is proportional to the applied voltage. As discussed above, floating anode 110 must support half the total working voltage on the side facing cathode 120 and must have a barrier oxide layer formed on this side. The side facing powered anode 130 does not need to support voltage and should not be formed. A barrier oxide layer is also formed on powered anode 130 and powered anode 130 supports a second half of the total working voltage of the capacitor.

After the forming step, the anode plates are stamped and removed from the anode foil at step 226 using conventional matched metal dies, or other cutting and punching methods known to those skilled in the art.

A plurality of powered and floating anode plates are assembled with cathode plates and separators, according to the powered anode/floating anode/cathode arrangement of the present invention, into a stacked or layered capacitor assembly at step 228. The stacked capacitor unit is impregnated with a solvent-based liquid electrolyte and then placed in a capacitor case, such as a sealed aluminum casing. Using a small current source, the entire unit is aged to 800V, by slowly increasing the voltage on the capacitor after impregnation with electrolyte over the course of many hours. After reaching the maximum rated voltage, the voltage is decreased and the temperature increased. Alternatively, the assembly step may be performed by placing the various layers directly into a portion of the capacitor housing which is later closed. Such an assembly method is described in U.S. Pat. No. 5,522,851 to Fayram, which patent is incorporated herein by reference. Alternatively, a capacitor housing may not be required when using a solid electrolyte where no capacitor case is required, such as described in U.S. Pat. No. 4,942,501 to MacFarlane et al., which patent is incorporated herein by reference.

Alternatively, a cylindrical or wound roll capacitor arrangement could be constructed in which very thin rolls of aluminum or other valve metal foil are used as the powered anode layer, floating anode layer and cathode layer, with separators interposed therebetween. The formed foil is rolled and then aged in the presence of an electrolyte to grow oxide on any exposed aluminum. The entire laminate is rolled up into the form of a substantially cylindrical body, or wound roll, held together with adhesive tape and encased, with the aid of suitable insulation, in an aluminum tube or canister. Connections to the anode and the cathode are made via tabs.

Electrolytic capacitors according to the present invention can be incorporated into implantable medical devices, such as implantable cardioverter defibrillators (ICDs), as would be apparent to one skilled in the art, as described in U.S. Pat. No. 5,522,851 issued to Fayram.

Having now generally described the invention, the same will be more readily understood through reference to the following examples which are provided by way of illustration, and are not intended to be limiting of the present invention.

EXAMPLE 1

To gain a better understanding of the design, open units were built according to the powered anode/floating anode/cathode arrangement of the present invention. The electrolyte was dripped onto the parts as assembled. The floating anode was large enough that electrolyte could not wick around its edge to give a low impedance path from powered anode to the cathode. With this construction, the floating anode could be probed. The electrolyte could also be probed on either side of the floating anode.

An 800 V unit was built using an 800 V electrolyte. Nonporous, high strength, high voltage anode foil (no seepage in 100 sec) was used as the floating anode, a standard 300 AF porous high gain anode foil (allowing 23 m] of $H_2O$ to pass in 100 seconds) was used as the powered anode and a 20 $\mu$m nonporous cathode foil (no seepage in 100 sec) was used as the cathode. The anode foils were etched in a etch solution containing 0.62% HCl, 3.5% $NaClO_4$ and 5% $H_2SO_4$. The foils were etched at a temperature of 88° C. and a current density of 0.25 $A/cm^2$. The foils were then widened in a standard widening solution mixed with $HNO_3$ at a current density of 0.15 $A/cm^2$. After cleaning the etched and widened foils in deionized water, a barrier oxide layer was formed on the anode foil surface. The anode foil was formed to 940 volts at a current of 0.4 A in dimethylamine sebacate (DMAS) at room temperature. The foils were then treated in a 2% $H_3PO_4$ solution for 4 min at 70° C. The anode foil was reformed in DMAS to 900 V at a current of 0.1 A. To ensure healthy oxide formation on the floating anode, the floating anode was aged to 400 V, then the entire unit was aged to 800 V. The anodes were sealed with hot glue.

It was found that about 450 V was dropped from the cathode to floating anode, the remaining 350 V dropped between the powered anode and floating anode. The capacitance was about 0.7° F. for a 4 $cm^2$ device.

EXAMPLE 2

The total capacitance for the powered anode/floating anode/cathode capacitor construction discussed above can be calculated using the following formula:

$$\frac{1}{C_{total}} = \frac{1}{C_c} + \frac{1}{C_{af}} + \frac{1}{C_{cf}} + \frac{1}{C_a}$$

assuming equal surface area for each foil, where:

$C_{total}$=total capacitance per square centimeter $C_c$=cathode capacitance $C_{af}$=floating anode effective capacitance
 (Approximately ½ the foil capacitance because it is non-porous)

$C_{cf}$=capacitance of the cathode foil bonded to the floating anode $C_a$=capacitance of the anode foil $C_a$ and $C_{af}$ must support approximately 400 V each so they must have a barrier oxide layer formed on them.

$C_c$ and $C_{cf}$ need not support high voltage and thus can have very high capacitance values, essentially dropping out of the inverse capacitance equation above.

Preferably, an 8 cm² of non porous high strength, high voltage anode foil is used for the floating anode at approximately 0.81 μF/cm². Since only one side of the floating anode is used as an anode, only half of the capacitance is obtained. Thus: $C_{af}$=8 cm²×0.4 μF/cm²3.2 μF.

Preferably a 4 cm² of porous anode foil is used for the powered anode at approximately 1.2 μF/cm². Thus: $C_a$=4 cm²×1.2 μF/cm²=4.8 μF/cm². Therefore, $$\frac{1}{C_{total}} \approx \frac{1}{C_{af}} + \frac{1}{C_a} = \frac{1}{3.2\ \mu F} + \frac{1}{4.8\ \mu F}$$

$$C_{total} = 1.92\ \mu F$$

Actual values obtained are as follows:

| | |
|---|---|
| floating anode to powered anode | C = 4.49 μF ESR = 88.9 Ω |
| cathode to floating anode | C = 3.15 μF ESR = 149.2 Ω |
| cathode to powered anode | C = 1.85 μF ESR = 236.2 Ω |

In this construction, only one side of the floating anode foil is utilized. The lack of porosity limits the effective surface area to the side facing the cathode. It is possible to gain capacitance back by using porous foil for the floating anode, but then one side of the floating cathode must be formed to 400 V. This may be occurring already in this construction due to what minimal porosity the anode foil has. This could be responsible for the relatively high leakage observed between the cathode and floating anode.

As shown by this experiment, in terms of capacitance per thickness-per cm², this construction could yield (assume double anode):

| | |
|---|---|
| cathode foil | 4 × 20 μm |
| anode foil | 2×105 μm ⇒ $C_a$ = 2.4 μF/cm² |
| floating anode foil | 2×100 μm ⇒ $C_{af}$ = 0.8 μF/cm² |
| paper pad | 4 × 20 μm |
| This yields | $\frac{0.6\ \mu F}{cm^2\ 570\ \mu m} = .00105 \frac{\mu F}{cm^2\ \mu m} = 10.5 \frac{\mu F}{cc}$ |

If standard 300 μF porous high gain anode foil is used for the floating anode instead of the non porous high strength, high voltage anode foil, then: floating anode foil 2×105 μm →$C_{af}$=2.4 μF/cm² and $$\frac{1.2\mu F}{cm^2\ 580\ \mu m} = .00207 \frac{\mu F}{cm^2\ \mu m} = 20.7 \frac{\mu F}{cc}$$

In comparison, a conventional two 400 V capacitors in series arrangement yields:

| | |
|---|---|
| cathodes | 4 × 20 μm |
| paper | 4 × 20 μm |
| anode | 2 × 105 μm ⇒ 2.4 μF/cm², two in series |
| This gives | $\frac{1.2\ \mu F}{cm^2\ 580\ \mu m} = 20.7 \frac{\mu F}{cc}$ |

As can be seen from the above, the conventional two capacitors in series arrangement used in conventional ICD manufacture can be replaced with a single capacitor having the powered anode/floating anode/cathode arrangement of the present invention. Thus, the capacitor of the present invention solves the need for a capacitor arrangement for an ICD in a single package capable of operating at a voltage of 700 to 900 volts.

All references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for making an electrolytic capacitor comprising the steps of:

providing a thin metallic powered anode foil and a thin metallic floating anode foil;

etching said powered anode foil and said floating anode foil to provide enhanced surface area;

forming an oxide layer on said powered anode foil and said floating anode foil;

providing a plurality of separators and a thin metallic cathode foil; and rolling said anode foils, said cathode foil and said separators into a substantially cylindrical wound roll such that said floating anode plate is disposed between said cathode plate and said powered anode plate and said separators are disposed therebetween.

2. The method of claim 1, further including enclosing the assembly in a housing.

3. The method of claim 1, further including the step of impregnating said capacitor with an electrolyte.

4. A process for making an electrolytic capacitor comprising the steps of:

providing a first thin metallic anodic foil and a second thin metallic anodic foil;

etching said first anodic foil and said second anodic foil to provide enhanced surface area;

forming an oxide layer on said first anodic foil and said second anodic foil;

cutting and removing a powered anode plate from said first anodic foil and cutting and removing a floating anode plate from said second anodic foil;

providing a plurality of separators and a cathode plate; and stacking said plates and separators such that said floating anode plate is disposed between said cathode plate and said powered anode plate and said separators are disposed therebetween.

5. The method of claim 4, further including enclosing the assembly in a housing.

6. The method of claim 4, further including the step of impregnating said capacitor with an electrolyte.

* * * * *